US012359231B2

(12) United States Patent
Godart et al.

(10) Patent No.: US 12,359,231 B2
(45) Date of Patent: Jul. 15, 2025

(54) OIL OF MICROORGANISMS RICH IN DOCOSAHEXAENOIC ACID

(71) Applicant: FERMENTALG, Libourne (FR)

(72) Inventors: Francois Godart, Vayres (FR); Adeline Lapendrie, Bonzac (FR)

(73) Assignee: FERMENTALG, Libourne (FR)

( * ) Notice: Subject to any disclaimer, the term of this patent is extended or adjusted under 35 U.S.C. 154(b) by 0 days.

(21) Appl. No.: 18/498,807

(22) Filed: Oct. 31, 2023

(65) Prior Publication Data

US 2024/0141395 A1  May 2, 2024

Related U.S. Application Data

(63) Continuation of application No. 17/275,867, filed as application No. PCT/EP2019/074458 on Sep. 13, 2019, now abandoned.

(30) Foreign Application Priority Data

Sep. 14, 2018 (FR) ........................ 1858292

(51) Int. Cl.
| | |
|---|---|
| *C12P 7/6472* | (2022.01) |
| *A23L 33/115* | (2016.01) |
| *C12N 1/10* | (2006.01) |
| *C12R 1/90* | (2006.01) |

(52) U.S. Cl.
CPC ........... *C12P 7/6472* (2013.01); *A23L 33/115* (2016.08); *C12N 1/105* (2021.05); *C12R 2001/90* (2021.05)

(58) Field of Classification Search
None
See application file for complete search history.

(56) References Cited

U.S. PATENT DOCUMENTS

| | | | |
|---|---|---|---|
| 6,750,048 B2 | 6/2004 | Ruecker et al. | |
| 2005/0170479 A1 | 8/2005 | Weaver et al. | |
| 2011/0295028 A1 | 12/2011 | Cherinko et al. | |
| 2014/0100280 A1 | 4/2014 | Anderson | |
| 2014/0323569 A1* | 10/2014 | Raman | A23L 31/00 426/601 |
| 2014/0350222 A1 | 11/2014 | Zhang et al. | |
| 2015/0176042 A1 | 6/2015 | Dennis et al. | |
| 2015/0176072 A1 | 6/2015 | Wang et al. | |
| 2016/0319218 A1 | 11/2016 | Leininger et al. | |
| 2017/0016036 A1 | 1/2017 | Calleja et al. | |
| 2017/0335356 A1 | 11/2017 | Burja et al. | |

FOREIGN PATENT DOCUMENTS

| | | |
|---|---|---|
| CN | 1703516 A | 11/2005 |
| CN | 101519676 A | 9/2009 |
| CN | 101528067 A | 9/2009 |
| CN | 103354839 A | 10/2013 |
| CN | 104011218 A | 8/2014 |
| CN | 104745486 A | 7/2015 |
| EP | 0223960 A2 | 6/1987 |
| EP | 1001034 A1 | 5/2000 |
| FR | 1186824 A | 9/1959 |
| JP | 2010-136730 A | 6/2010 |
| WO | 1994/008467 A1 | 4/1994 |
| WO | 1997/037032 A2 | 10/1997 |
| WO | 2001/054510 A1 | 8/2001 |
| WO | 02/10322 A1 | 2/2002 |
| WO | 03/049832 A1 | 6/2003 |
| WO | 2010/107415 A1 | 9/2010 |
| WO | 2011/153246 A2 | 12/2011 |
| WO | 2012/035262 A1 | 3/2012 |
| WO | 2013/136025 A1 | 9/2013 |
| WO | 2013/136028 A1 | 9/2013 |
| WO | 2014/146098 A1 | 9/2014 |
| WO | 2015/004402 A2 | 1/2015 |
| WO | 2015/004403 A2 | 1/2015 |
| WO | 2015/095688 A1 | 6/2015 |
| WO | 2015/095694 A1 | 6/2015 |
| WO | 2015/150716 A2 | 10/2015 |
| WO | 2016/060631 A1 | 3/2016 |
| WO | 2017/094804 A1 | 6/2017 |
| WO | 2018/011275 A1 | 1/2018 |

OTHER PUBLICATIONS

Raghukumar, Thraustochytrid Marine Protists: Production of PUFAs and other emerging technologies, Mar. Biotechnol. 10:631-640, Aug. 2008.
Yokoshi et al., Optimization of docosahexaenoix acid production by Schuzochytrium limacinum SR21, Appl. Microbiol. Biotechnol. 49:72-76, Jan. 1998.
Hadaruga et al., Thermal and oxidative stability of Atlantic salmon oil (*Salmo sair* L.) and complexation with B-cyclodextrin, Beilstein. J. Org. Chem. 12:179-191, Feb. 2016.
Lin et al., Optimization of Enzymatic Cell Disruption for Improving Lipid Extraction from Schizochytrium so. through Response Surface Methodology, J. Oleo Sci. 67:215-224, Jan. 2018.
Yel et al., Comparison of Cell Disruption and Liped Extration Methods for Improving Lipied Content of *Schizochytrium* sp. S31, J. Mol. Biol. Biotechnol. 1:9-12, Apr. 2017.
Veynachter et al., Centrifugation et décantation, Techniques de l'ingénieu F2730, Mar. 20007.
Pages et al., Raffinage des huiles et des corps gras et élimination des contaminants, OCL 17:86-99, Mar. 2010.
Jin et al., Enzyme-assisted extraction of lipids directly from the culture of the oleaginous yeast *Rhodosporidium toruloides*, Bioresource Technology 111:378-382, Feb. 2012.
Fedorova-Dahms et al., Safety evaluation of DHA-rich algal oil from *Schizochytrium* sp, Food and Chemical Toxicology, 2011, vol. 49, 3310-3318.

(Continued)

*Primary Examiner* — Blaine Lankford
(74) *Attorney, Agent, or Firm* — BCF LLP

(57) ABSTRACT

The present invention relates to an oil of microorganisms rich in docosahexaenoic acid (DHA, C22:6n3), comprising more than 60% of DHA relative to the total mass of fat and to the use thereof for human or animal feed, in particular for feeding infants, children, or pregnant or lactating women.

21 Claims, No Drawings

(56) References Cited

OTHER PUBLICATIONS

Folch et al., A simple method for the isolation and purification of total lipides from animal tissues, J. Biol. Chem., 1957, vol. 226, No. 1, 497-509.

Hamilton et al, Heterotrophic production of Omega-3 long-chain polyunsaturated fatty acords by trophically converted marine diatom pharodactylum tricnornum, Marine Drugs, 2016, vol. 14, No. 53, 1-10.

Ghasemifard et al, Omega-3 long chain fatty acid "bioavailability": a review of evidence and methodological considerations, Progress in Lipid Research, 2014, vol. 56, 92-108.

Tsuzuki, Study of the formation of trans fatty acids in models oils (triacylglycerols) and edible oils during the heating process, JARQ, 2012, vol. 46, No. 3, 215-220.

Miyazaki et al., An improved enzymatic indirect method for simultaneous determinations of 3-MCPD esters and glycidyl esters in fish oils, Journla of Oleo Science, 2017, 66(10), p. 1085-1093.

Jouhet et al., Transient increase of phosphatidylcholine in plant cells in response to phosphate deprivation, FEBS Letters 544, 2003, 63-68.

Mansour et al., Characterization of oilseed lipids from "DHA-Producting Camelina sativa": A new transformed land plant containing long-chain Omega-3 oils, Nutrients, 2014, vol. 6, No. 2, 776-789.

Ruiz-Lopez et al., Successful high-level accumulation of fish oil Omega-3 long chain polyunsaturated fatty acids in a transgenic oilseed crop, The Plant Journal, 2014, vol. 1=77, No. 2, 198-208.

Rosenthal et al., Aqueous and enzymatic processes for edible oil extraction, Enzyme and Microbial Technology, 1996, vol. 19, 402-420.

FDA, Gras Notice No. 836, Dec. 2018, https://www.fda.gov/food/generally-recognized-safe-gras/gras-notice-inventory; https://www.fda.gov/media/132949/download.

NIH, Spring Valley Algal-900 DHA (Label), NIH Office of Dietary Supplements, Dietary Supplement Label Database (DSLD), Oct. 25, 2012, https://dsld.od.nih.gov/label/13039.

* cited by examiner

OIL OF MICROORGANISMS RICH IN DOCOSAHEXAENOIC ACID

CROSS-REFERENCE TO RELATED APPLICATIONS

The present application is a Continuation application of U.S. patent application Ser. No. 17/275,867, filed on Mar. 12, 2021, which is a national phase entry of PCT International Application No.: PCT/EP2019/074458, filed on Sep. 13, 2019, which claims priority to French Patent Application No. 1858292, filed on Sep. 14, 2018; all of which are incorporated by reference herein in their entirety.

FIELD OF THE INVENTION

The present invention relates to an oil of microorganisms rich in docosahexaenoic acid (DHA, C22:6n3), comprising more than 60% DHA in relation to the total mass of fat and at least 80% triglycerides in relation to the total mass of fat.

STATE OF THE ART

Oils containing DHA come from several sources, the most well known are fish, krill and microorganisms such as microalgae. Many strains of microorganisms are known to produce PUFAs, in particular docosahexaenoic acid (DHA), arachidonic acid (ARA) or eicosapentaenoic acid (EPA), also identified by the signs ω3 and ω6. These PUFAs are widely used in industry, in particular for human or animal food, or in cosmetics, and their industrial production has been continuously improved for many years (WO 1997/037032, WO 2001/054510, WO 2013/136028, WO 2015/004402, US 2017/016036, US 2017/335356). The criteria for selecting strains suitable for industrial production are their high biomass productivity, a significant accumulation of triglycerides (TG) and a high PUFA content in the fat. Today, many known industrial strains meet these first three criteria, with a PUFA content in the fat of the order of 35%, or even 50% in the best case.

However, there is a demand for concentrated oils with high PUFA contents, namely for the supply of concentrated products such as concentrated oil capsules that make it possible to reduce the number of unit doses needed for an equivalent quantity of PUFA. To obtain oils with a high PUFA content (for example above 55% DHA), the oils can be enriched by adding PUFA (US 2014/323569) and/or the oils are concentrated by a process that converts triglycerides to ethyl esters involving the use of solvent such as ethanol. Ethyl esters are an artificial chemical form, they do not exist in nature. The bioavailability of fatty acids in the form of ethyl esters is much less than in the form of triglycerides (Ghasemifard et al., 2014). Moreover, the process removes the vitamins and antioxidants present in the crude oil. Consequently, the concentrated oil is more vulnerable to oxidation.

It is possible to convert these ethyl esters back to triglycerides, these are "reformed" triglycerides, in order to improve bioavailability. Antioxidants can also be added to increase the stability of the oil over time. However, this concentrated oil is rather different from the natural oil, it has undergone a number of transformation processes that have changed its composition: fatty acid profile, vitamins, pigments and other antioxidant molecules, depriving the PUFAs of their natural protection. However, PUFAs are sensitive, in particular temperature-sensitive, molecules which can convert cis bonds to trans bonds (Tsuzuki W, 2012). It should also be noted that the re-formation of triglycerides is incomplete, the oil thus treated still contains a variable proportion of ethyl esters, which distinguishes it from untreated oil. The ethanol released during transesterification (conversion of ethyl esters to triglycerides) is generally removed by evaporation. Nevertheless, traces of ethanol remain in the concentrated oil.

Another reason for wanting to minimize oil treatment processes is the formation of contaminants such as monochloropropanediols (2-MCPDs, 3-MCPDs) and glycidol and derivatives thereof (2-MCPD, 3-MCPD and glycidol fatty acid esters). The presence of these contaminants has been detected in particular following the steps of purification and deodorization of fish oil (Miyazaki and Koyama, 2017). There is at present little data available concerning the impact of concentration processes on the formation of contaminants. However, the re-formation of triglycerides from ethyl esters may lead to an increase in diglycerides, which are contaminant precursor compounds. The level of glycidol (and glycidol esters) is subject to regulation (EU) 2018/290/EC to limit its content in foods: the concentration must not exceed 1000 µg/kg in edible oils except for edible oils intended for the preparation of foods for babies and infants where the limit is 500 µg/kg. In preparations for babies and infants, the maximum level is even lower: 75 µg/kg in powders and 10 µg/kg in liquids. This level will be further reduced (50 and 6 µg/kg, respectively) in 2019. The evaluation of maximum MCPD concentrations is currently underway for oils and baby foods. For the moment, the regulation relates only to hydrolyzed vegetable proteins and soy sauce (limit of 20 µg/kg).

It is therefore of interest to obtain an oil naturally rich in PUFAs, the composition of which is as close as possible to the liposoluble substances of the producing microorganism, with a minimum of contaminants produced during treatments. This makes it particularly suited to the integration of DHA in food products. Its very low 3-MCPD and glycidol content, combined with its high DHA content, makes it ideal for the preparation of foods intended for babies and infants.

Moreover, these concentrated oils are generally obtained by treatment processes which are expensive and harmful to the environment.

Another known solution consists in generating genetically modified microorganisms to seek to promote the metabolic pathways of PUFA production (Hamilton & al., 2016) or mutants believed to produce more DHA (WO 2017/09804). However, the choice of technical solutions is limited by the use made of the oils obtained, in particular in human food (Fedorova-Dahms I. & al., 2011).

There is a need for oils naturally concentrated in PUFA, which require no treatments other than extraction methods, i.e., for which PUFAs are essentially in the form of triglycerides as produced by microorganisms. More particularly, there is a need for oils with a high PUFA content and a lower saturated fatty acid content. In addition to the question of oil quality, the interest in a low saturated fatty acid content is moving toward a less viscous oil, easier to use at industrial levels, in particular requiring less energy for its handling.

The invention meets this demand with an oil with a high DHA content, comprising at least 60% DHA in relation to the total mass of fat. This oil contains neither ethyl esters nor traces of solvent (ethanol or methanol) and has a reduced content of 3-MCPD and glycidol (compared with oils containing more than 60% DHA currently on the market).

DISCLOSURE OF THE INVENTION

The present invention relates to a microbial oil which comprises docosahexaenoic acid (DHA), characterized in that it comprises at least 80% triglycerides in relation to the total mass of fat, more than 60% DHA in relation to the total mass of fat and the saturated fatty acid content is less than 25% in relation to the total mass of fat.

It also relates to a diluted microbial oil which comprises a microbial oil rich in triglycerides and in DHA according to the invention, mixed with another oil.

Another object of the invention is a biomass of microorganisms that comprises an oil rich in triglycerides and in DHA according to the invention.

The invention also relates to the use of an optionally diluted oil rich in triglyceride and in DHA according to the invention or of a biomass that contains this oil for human or animal food, in particular for food for newborns, children, or pregnant or nursing women.

Another object of the invention is a food, characterized in that it comprises an optionally diluted oil rich in triglycerides and in DHA according to the invention.

DETAILED DESCRIPTION OF THE INVENTION

The oil according to the invention is a microbial oil which comprises more than 60% DHA in relation to the total mass of fat, advantageously at least 62% DHA, more advantageously at least 65% DHA, preferably more than 67%, more preferentially at least 70%, even more preferentially 75% DHA in relation to the total mass of fat.

These characteristics of the oil according to the invention concern both the oil as present in the biomass of microorganisms and the oil extracted from this biomass, whether crude or purified.

The invention also relates to a diluted oil, comprising the oil according to the invention mixed with another oil.

The invention also relates to a pharmaceutical, cosmetic or food composition that comprises an oil according to the invention, whether crude, refined or diluted.

The invention also relates to the use of an oil according to the invention, crude, refined or diluted, or a biomass containing the oil, for human or animal food, in particular food for newborns, children, or pregnant or nursing women.

DETAILED DESCRIPTION OF THE INVENTION

The oil according to the invention is an oil of microbial origin, obtained from a biomass of microorganism cells grown under conditions allowing both cell growth (to produce the biomass) and the production of an oil with a high DHA content.

The oil according to the invention is a microbial oil which comprises more than 60% DHA in relation to the total mass of fat, advantageously at least 62% DHA, more advantageously at least 65% DHA, preferably more than 67%, more preferentially at least 70%, even more preferentially at least 75% DHA in relation to the total mass of fat.

Preferably the oil according to the invention has a high content of unsaturated fatty acids in relation to saturated fatty acids. The unsaturated fatty acids in the oil according to the invention are essentially DHA and DPA (docosapentaenoic acid, C22:5n6). The ARA (arachidonic acid, C20:4n6) content is generally less than 0.5%, or even less than 0.3%, advantageously less than 0.1%. The EPA (eicosapentaenoic acid, C20:5n3) content is generally less than 1.5%, advantageously less than 1%, more advantageously less than 0.5%. The percentages of ARA and EPA are given in relation to the total mass of fat.

Advantageously, the combined DHA and DPA content is at least 70% in relation to the total mass of fat, advantageously at least 75%, more advantageously at least 80%, and even more advantageously at least 85% in relation to the total mass of fat. In certain cases, total DHA+DPA represents up to 90% of the total mass of fat. For the oils with the highest DHA content, at least 70%, the combined DHA and DPA content is at least 80%, preferentially at least 85%.

For a DHA-rich oil according to the invention, the DHA/DPA ratio is preferably at least 3, more preferentially at least 4, ranging from 4 to 9. For the oils with the highest DHA content, at least 70%, the DHA/DPA ratio is advantageously from 4 to 7.

The saturated fatty acid content is less than 25% in relation to the total mass of fat, or even less than 20%, more preferentially less than 15%, even more preferentially less than 10%.

The saturated fatty acids are essentially palmitic acid (C16:0). Other saturated fatty acids are present in a content less than 2%, or even less than 1%, in particular pentadecylic acid (C15:0) or myristic acid (C14:0) or stearic acid (C18:0). Advantageously, C10 to C22 saturated fatty acids other than palmitic acid are, independently of each other, present in trace amounts, each in a content of less than 0.1%, or even absent (0% taking into account the uncertainties of the methods of analysis), in particular for C10, C11, C12, C17, C20, C21 and C22 saturated fatty acids. The percentages are given in relation to the total mass of fat.

The palmitic acid content is preferably less than 20% of the total mass of fat, more preferentially less than 15%, even more preferentially less than 10%.

For the oils with the highest DHA content, at least 70%, the C10 to C22 saturated fatty acid content is preferably less than 15%, more preferentially less than 10%.

One way to measure the high DHA content of the oil according to the invention and the low saturated fatty acid (SFA) content is to establish a DHA/SFA ratio.

It is advantageously at least 2.5, preferentially at least 3, more preferentially at least 5, even more preferentially at least 6. It may go up to at least 8 in some cases, or even at least 9. For the oils with the highest DHA content, at least 70%, the DHA/SFA ratio is at least 4, preferentially at least 6, more preferentially at least 8, up to about 9.

It is also possible to measure the high content of polyunsaturated fatty acids in relation to saturated fatty acids (SFA) by the (DHA+DPA)/SFA ratio.

It is advantageously at least 2.5, preferentially at least 3, more preferentially at least 4, even more preferentially at least 5. It may go up to at least 8 in some cases, or even at least 9. For the oils with the highest DHA content, at least 70%, the (DHA+DPA)/SFA ratio is at least 5, preferentially at least 7, more preferentially at least 10, up to about 11 or more.

The oils according to the invention are essentially in the form of triglycerides. Triglycerides represent at least 80% of the total mass of fat, advantageously at least 90%, more advantageously at least 93% of the total mass of fat. The triglyceride content is for example analyzed by thin-layer chromatography (Jouet et al., 2003).

These characteristics of the oil according to the invention concern both the oil as present in the biomass of microorganisms and the oil extracted from this biomass, whether crude or purified.

In certain cases, depending on the process used, the extraction of the oil from the biomass can lead to a slight increase in the DHA and DPA content, favoring the extraction of these PUFAs over saturated fatty acids of lower molecular weight. However, this concentration does not substantially modify the intrinsic properties of the oil contained in the biomass, in particular the triglyceride content. In all cases, the oil according to the invention is an oil that has not undergone substantial modifications of its fatty acid content by the addition of PUFA, for example in the form of esters, by concentration and/or by the removal of saturated fatty acids such as palmitic acid.

The oil according to a particular embodiment of the invention contains more than 10 mg of native carotenoids per kg of oil, or even more than 30 mg/kg, preferentially more than 40 mg/kg, even more preferentially more than 60 mg/kg, or even at least 65 mg/kg. The carotenoids present are predominantly astaxanthin and beta-carotenes. The oil contains more than 20 mg/kg of astaxanthin, or even more than 30 mg/kg, more preferentially more than 40 mg/kg. Canthaxanthin is also present but in smaller amounts. Other carotenoids such as lutein and zeaxanthin may be present but they are at the limit of detection of the method used. The term "native carotenoids" means that the carotenoids have not been added, they come from the same biomass as the oil and are extracted from this biomass at the same time as the oil. They are produced by the strain under heterotrophic fermentation conditions, with no particular stimulus. These native carotenoids are therefore present throughout the process, protecting the fatty acids, in particular DHA, against oxidation. The refining process can remove pigments, so the refined oil may contain fewer carotenoids, if any.

The color of the oil is usually evaluated by measuring the Gardner index, according to the method described in standard AOCS Cc 13j-97 (revised 2017) with a spectrophotometer. The measurement scale comprises 18 grades, ranging from transparent (1) to dark red/brown (18). Some carotenoids, including astaxanthin and beta-carotenes, show a coloration, more or less intense depending on their concentration. Their presence is thus reflected in a higher Gardner index. The oil according to a particular embodiment of the invention has a Gardner index higher than 8 or even higher than 10, preferably between 12 and 17.

The Gardner scale is traditionally used to evaluate the aging of oils because the oxidation of oils rich in polyunsaturated fatty acids (PUFAs) can result in a yellowing of the color (for a transparent oil), thus a higher Gardner value. However, the oxidation of PUFA-rich oils is more precisely measured by the anisidine index and the peroxidation index. The oils according to the invention have both low anisidine and peroxide indexes, which guarantee a low oxidation product, and a high Gardner index, due to the presence of carotenoids. The oils according to the invention have an anisidine index of less than 5, or even less than 2, preferably less than 1.5, and a peroxidation index of less than 5, or even less than or equal to 1, preferably less than or equal to 0.5.

The oils according to the invention have a fairly low melting temperature, which decreases in correlation with the increase in DHA content. The melting temperature is measured according to standard ISO 6321. Indeed, the oils, with more than 600 mg of DHA/g of fatty acids (or about more than 62% DHA) have a melting temperature below 20° C., even less than or equal to 5° C. They are therefore liquid at room temperature. The oils with more than 700 mg of DHA per g of fatty acids (or about more than 73% DHA) have a melting temperature below −5° C. A low melting temperature facilitates storage and handling (pumping in particular), since it is possible to store the oil in liquid form while refrigerating it in order to limit aging. Oils that freeze during storage must be warmed up for sampling and for incorporation into mixtures. However, temperature is a factor that accelerates oxidation.

This property is also reflected in the viscosity value, measured by a viscometer at 22° C. (Viscoman, Gilson). The oils according to the invention have a viscosity value at room temperature of less than or equal to 50 Pa·s, or even of less than 40, preferably of less than 30.

The oils according to the invention are obtained by culturing microorganisms that produce DHA-rich oils. The strains of microorganisms which make it possible to obtain such oils are industrial strains, i.e., according to the invention, strains the fat content of which represents at least 45% of the dry matter, preferentially at least about 50% of the dry matter, and which have a growth capacity at a cell density of at least 50 g/L, preferably at least 70 g/L, more preferentially at least 100 g/L.

The person skilled in the art is familiar with industrial strains of PUFA-producing microorganisms mainly among thraustochytrids, dinoflagellates, diatoms, eustigmatophytes, in particular microorganisms of the genera *Crypthecodinium, Schizochytrium, Thraustochytrium* or *Aurantiochytrium* for the production of DHA.

The analysis of PUFA content in the fat is carried out according to the standard methods of the skilled person, in particular described in the following article: Gas Chromatographic Quantification of Fatty Acid Methyl Esters: Flame Ionization Detection vs. Electron Impact Mass Spectrometry, Dodds et al., Lipids, Vol. 40, no. 4 (2005).

More particularly, mention may be made of the strains *Aurantiochytrium mangrovei* CCAP4062/7 and CCAP4062/8 and *Schizochytrium* sp. CCAP4087/7 which produce oils comprising more than 60% DHA in relation to the total mass of fat. The invention also relates to those strains capable of producing oils comprising more than 60% DHA.

The processes for the industrial culture of microorganisms for the production of a fermenting must which will then be used to produce oil are well known to the person skilled in the art, whether in autotrophic, heterotrophic or mixotrophic mode. Industrial culture in heterotrophic or mixotrophic mode allows cell densities of at least 50 g/L, preferentially at least 70 g/L, more preferentially at least 100 g/L.

According to the invention, "industrial culture" means a culture of the strains in a culture medium suitable for their growth and for PUFA production and in a volume suitable for the production of sufficient amounts to address a market.

These industrial cultures are carried out by fermentation in a discontinuous "batch" mode, a semi-continuous "fed batch" mode or a continuous mode. The fermenters have volumes which can range from 1000 L to more than 200 m³.

The suitable culture medium is preferably a chemically defined culture medium that comprises a carbon source, a nitrogen source, a phosphorus source and salts. "Chemically defined culture medium" means a culture medium in which the content of each element is known. Advantageously, the medium does not include rich or complex organic matter. Rich or complex organic matter means unpurified organic matter in the form of mixtures for which the exact composition and concentrations of the various components of the mixture are not accurately known, not controlled, and may show significant variability from batch to batch. As examples of rich or complex organic matter, mention may be made of yeast extracts or peptones which are products of a protein hydrolysis reaction, or rich mineral matter such as marine mineral salts or other complex growth agents, not having a fixed concentration of each of their components.

Generally, industrial culture processes comprise a growth step to promote biomass production, followed by an accumulation step to promote the production of fat and PUFA in particular. This is notably the case for the process described in patent application WO 2001/054510. More recently, processes have been described using culture conditions that concomitantly promote the production of biomass and that of PUFA. Particular mention may be made of the culture methods described in applications WO 2012/035262, WO 2015/004402 and WO 2015/004403. Of course, the skilled person will be able to adapt the culture conditions, in particular the composition of the medium, the conditions for adding nutrients during the culture, the temperature, oxygenation cycles and the lighting conditions to promote biomass production.

The temperatures of industrial culture are advantageously greater than 17° C.

According to the invention, "biomass" advantageously means a set of microorganism cells produced by their culture, in particular by the methods described above, cells which may or may not have retained their physical integrity. It is therefore understood that said biomass may include a quantity of degraded microorganism cells from 0% to 100%. "Degraded" means that the physical integrity of said microorganism cells may have been altered, such as lysed microorganisms, resulting for example from a process of homogenization or enzymatic lysis. Once produced, this biomass can be raw, just separated from its culture medium, dried or not, degraded or not.

The biomass, depending on whether it is dried or not, totally or partially, can have a moisture content of 1% to 90%.

The invention therefore also relates to a biomass of microorganisms comprising an oil as previously defined.

According to a first embodiment, the biomass has a moisture content of 70% to 90%, preferentially 80% to 85%. This is particularly the case when it essentially consists of optimized industrial microorganisms cultivated after filtration of the fermenting must to separate the cultivated microorganisms from the culture medium, before drying.

According to another embodiment of the invention, the biomass is dried, totally or partially, and has a moisture content of 1% to 10%, preferentially 2% to 7%.

The biomass may be packaged for storage or for use as such, for example as a food supplement or food for human or animal consumption.

The methods for isolating an oil according to the invention from a biomass produced by the culture of microorganisms are well known to the person skilled in the art. Particular mention may be made of solid-liquid extraction which is based on the use of a solvent (liquid phase) to extract the oil contained in the dried biomass (solid phase) by sprinkling or maceration; liquid-liquid extraction which is based on the separation of the aqueous phase from the oil after preliminary lysis of the cells and then decanting or centrifugation. Preferably the extraction is done without organic solvents. Particular mention may be made of the applications WO 01/53512, WO 02/10423, WO 2014/122092, WO 2015/092546 and WO 2015/095694.

Mention may also be made of a preferred method for improving the fat extraction yields from microorganisms for PUFA-rich oils. This method consists in carrying out cell lysis at a first temperature, the latter being continued at a second temperature lower than the first, then mechanical separation of the oil from the lysed biomass (filtration, decanting).

Cell lysis is done by enzymatic or mechanical lysis (grinding). The temperature of the first part of lysis is preferably at least 50° C. while remaining below temperatures that would degrade the composition of the oils in addition to promoting cell lysis, i.e., temperatures below 80° C., preferably at most 70° C.

The enzymes that may be used are known, in particular described in WO2015/095688, WO2011/153246, U.S. Pat. No. 6,750,048 and WO2015/095694, in particular proteases or cellulases such as the enzymes marketed by the firm Novozyme under the names Alcalase 2.5 L, Alcalase 2.4 L, Novozym 37071, Flavourzyme 1000 L, Novozym FM 2.4 L, Protamex, Viscozyme. The conditions of use are those recommended by the supplier, the temperature being that recommended for optimal enzyme activity, at least 50° C. and up to 70° C., preferably about 65° C. Advantageously, enzymatic lysis is carried out in an oxygen-poor atmosphere.

Mechanical lysis methods are also well known, in particular by ball mill, mixer-disperser, high-pressure homogenizer pin mill or impact mill, ultrasonic, pulsed electric fields. Particular mention may be made for the ball mill: Netzsch/Discus-1000; WAB/ECM-AP60; for the high-pressure homogenizer: GEA/Ariete; for the mixer-disperser: Silverson/700-X, for the pin mill: Hosakawa/Contraplex; for the impact mill: Netzsch/Condux.

The first part of the lysis is carried out under the usual conditions recommended by the state of the art for cell lysis, in particular in terms of the duration of the enzymatic lysis or the grinding cycles.

The lysis continuation step completes the lysis by modifying the implementation conditions without having to extract the lysed biomass beforehand. The lysis temperature in this second part is at least 10° C. lower than that of the first part. Preferably, the temperature of the second part of lysis is less than or equal to 40° C., advantageously ranging from 5° C. to 40° C. This second part of lysis at a lower temperature, or end of lysis, is advantageously carried out for at least 30', advantageously up to 30 h.

The mechanical separation of an oil from a lysed biomass is also well known to the skilled person, as a gravity separation, in particular by centrifugation as described in patent application WO 01/53512. It is also possible to use continuous separation, in particular by centrifugal plate separator. Such separators are known to continuously extract oils from complex media comprising solid residues and water, as described in patent application WO 2010/096002, in particular marketed by the companies Alfa Laval, Flottweg or SPX Flow Technology Santorso, among others. This continuous separation step is preferred in the process used to obtain the oil according to the invention.

The oil obtained is generally an oil called crude oil, which can be used as is or can be refined, in particular to facilitate its storage, by preventing it from becoming rancid, or to change its color so as to make it more acceptable to a consumer. These refining steps are well known to the person skilled in the art, in particular degumming, clarification and deodorization. They remove (totally or partially) phospholipids, pigments, volatiles and free fatty acids. In fact, these methods do not substantially modify the relative content of fatty acids, saturated or unsaturated, nor the triglyceride content of the refined oil obtained compared with the crude oil.

The invention also relates to a packaged oil comprising a container of suitable volume to contain said oil, the oil being a DHA-rich oil as previously defined, crude or refined, and packaged in a quantity of oil greater than 1 L, advantageously in a quantity of oil greater than 10 L, more particularly in a quantity of oil of the order of 220 L, and more particularly in a quantity of oil of the order of 20 m³.

Any container capable of holding the volume of oil or biomass and protecting them for their storage and transportation may be used by the person skilled in the art. Advantageously, the volume of the container will be equal to or substantially greater than that of the oil or biomass packaged in such a way as to limit the presence of air in the container and limit oxidation. The container will be advantageously opaque in order to avoid the degradation of the product by light rays, in particular UV rays. Advantageously, the container will be airtight so that any volume not occupied with oil or biomass can be filled with an inert gas.

The oil according to the invention can be mixed with other oils for their final use. This dilution changes the overall content of DHA and other unsaturated fatty acids in the composition of the diluted oil. It remains possible, however, to identify in the final oil, in view of the fatty acid profile of the oil used for dilution, the relative percentages of fatty acids that come from the DHA-rich oil according to the invention and from the dilution oil.

The invention therefore also relates to a diluted oil, comprising the oil according to the invention mixed with another oil. The oils used to dilute the DHA-rich oil according to the invention are generally and preferably vegetable oils suitable for human or animal food consumption. Particular mention may be made of sunflower, rapeseed, soybean, walnut, sesame, hemp, hazelnut, argan, olive, linseed or any other oil suitable for food use. The added oil may also be an oil containing other PUFAs, in particular ARA and/or EPA, in particular other oils of microbial origin or fish oils.

The invention also relates to a composition that comprises an oil according to the invention, whether crude, refined or diluted, or that comprises the biomass according to the invention.

A composition according to the invention may comprise one or more excipients. An excipient is a component, or mixture of components, which is used in the present invention to give desirable characteristics to the composition for its storage and use, including foods and pharmaceutical, cosmetic and industrial compositions. An excipient may be described as a "pharmaceutically acceptable" excipient when it is added to a pharmaceutical composition whose properties are known from the pharmacopoeia to be used in contact with human and animal tissues without excessive toxicity, irritation, allergic reaction or other complications. Different excipients may be used such as an organic or mineral base, an organic or mineral acid, a pH buffer, a stabilizer, an antioxidant, an adhesion agent, a release agent, a coating agent, an outer phase component, a controlled release component, a surfactant, a humectant, a filler, an emollient, or combinations thereof.

Depending on their destination, the compositions according to the invention are in particular pharmaceutical, cosmetic, nutraceutical compositions or foods.

Foods are intended for both humans and animals and include solid, pasty or liquid compositions. Particular mention may be made of common foods, liquid products, including milks, beverages, therapeutic beverages and nutritional beverages, functional foods, supplements, nutraceuticals, preparations for infants, including preparations for premature infants, foods for pregnant or nursing women, foods for adults, geriatric foods and animal feeds.

The DHA-rich oil according to the invention, whether crude or refined, or the biomass containing it can be used directly as or added as an additive in an oil, a spread, another fat ingredient, a beverage, a soy-based sauce, dairy products (milk, yogurt, cheese, ice cream), bakery products, nutritional products, for example in the form of nutritional supplement (in capsule or tablet form), vitamin supplements, food supplements, powders to be diluted for beverages, such as energy drinks or milk powders for infant formulations, finished or semi-finished powdered food products, etc., according to the known uses of the person skilled in the art.

Animal feeds are also known to the person skilled in the art. They are in particular intended for farm animals, such as cows, pigs, chickens, sheep, goats or in fish farming for shellfish or farmed fish.

Pharmaceutical compositions comprising a DHA-rich oil are also known to the skilled person, the oil being used alone or in combination with other medicinal products.

The oil according to the invention, crude or refined, or the biomass containing it, may be formulated in the form of single-dose compositions, in particular in the form of tablets, capsules, powders, granules, suitable for oral administration.

The advantage of the DHA-rich oil according to the invention, whether crude or refined, or of the biomass containing it, is that it can be used in smaller amounts in these mixtures and compositions.

The invention also relates to the use of an oil according to the invention, crude, refined or diluted, or the biomass containing it, for human or animal food, in particular food for newborns, children, or pregnant or nursing women.

Such uses are well known to the person skilled in the art, in particular described in patent application WO 2010/107415 and on the website of the firm DSM (https://www.dsm.com/markets/foodandbeverages/en_US/products/nutritional-lipids/life-dha.html).

EXAMPLES

Example 1: Fatty Acid Profile of High DHA Content Biomass of Thraustochytrids

Strains of thraustochytrids (*Aurantiochytrium mangrovei*—FCCB1897, FCCB1800, CCAP4062/8) are grown in Erlenmeyer flasks in ATCC 790 (modified) culture medium. Similar results are obtained with strains of *Schizochytrium* sp. (in particular with strain CCAP4087/7).

Once the cultures are in the stationary phase, the biomass is recovered by centrifugation and then freeze-dried before analysis of the fatty acid composition of the biomass by GC-FID (method adapted from standard ISO 12966-2).

Composition of the modified ATCC 790 medium:

| | |
|---|---|
| Yeast extract | 5.0 g/L |
| Peptone | 5.0 g/L |
| D+-Glucose | 30.0 g/L |
| Sea salts | 20 g/L |

Table 1 represents the composition of fatty acids contained in the biomass. The results are expressed as a percentage of the total fatty acid content. SFAs are saturated fatty acids.

TABLE 1

| | FCCB1897 | FCCB1800 | CCAP4062/8 |
|---|---|---|---|
| C10:0 | 0.0 | 0.0 | 0.0 |
| C11:0 | 0.0 | 0.0 | 0.0 |
| C12:0 | 0.0 | 0.0 | 0.0 |
| C13:0 | 0.0 | 0.0 | 0.0 |
| C14:0 | 0.2 | 0.3 | 0.3 |

TABLE 1-continued

|  | FCCB1897 | FCCB1800 | CCAP4062/8 |
|---|---|---|---|
| C14:1 | 0.0 | 0.0 | 0.0 |
| C15:0 | 0.6 | 1.0 | 1.7 |
| C15:1 | 0.0 | 0.0 | 0.0 |
| C16:0 | 6.8 | 6.5 | 8.3 |
| C16:1 | 0.0 | 0.0 | 0.0 |
| C16:2 | 0.0 | 0.0 | 0.0 |
| C16:3 | 0.0 | 0.0 | 0.0 |
| C16:4 | 0.0 | 0.0 | 0.0 |
| C17:0 | 1.1 | 1.4 | 1.5 |
| C17:1 | 0.3 | 0.3 | 0.2 |
| C18:0 | 0.5 | 0.5 | 0.4 |
| C18:1 | 0.0 | 0.0 | 0.0 |
| C18:2 | 0.0 | 0.0 | 0.0 |
| C18:3n3 | 0.1 | 0.1 | 0.1 |
| C18:3n6 | 0.1 | 0.1 | 0.0 |
| C18:4n3 | 0.3 | 0.5 | 0.4 |
| C20:0 | 0.1 | 0.1 | 0.0 |
| C20:4n6 (ARA) | 0.3 | 0.3 | 0.3 |
| C20:5n3 (EPA) | 1.1 | 1.0 | 1.2 |
| C21:0 | 0.0 | 0.0 | 0.0 |
| C22:0 | 0.0 | 0.0 | 0.0 |
| C22:5n3 (DPAn3) | 0.4 | 0.3 | 0.4 |
| C22:5n6 (DPAn6) | 16.7 | 16.5 | 16.8 |
| C22:6n3 (DHA) | 70.9 | 70.9 | 68 |
| DHA + DPA | 88.0 | 87.8 | 85.2 |
| SFA | 7.7 | 7.8 | 10.2 |
| DHA/DPA | 4.2 | 4.2 | 4.0 |
| DHA/SFA | 9.2 | 9.1 | 6.7 |
| (DHA + DPA)/SFA | 11.4 | 11.3 | 8.4 |

Example 2: Fermenter Cultures of High DHA Content Strains

The cultures are carried out in fermenters (bioreactors) from 1 to 5 L useful with dedicated automated systems and supervision by computer station. They are carried out using two strains of *Aurantiochytrium mangrovei* and with two different culture protocols. The system is regulated at pH via the addition of base (NH$_4$OH for example b1 and b2 and with NaOH for example a) with pH adjustment carried out throughout the culture period, and providing a nitrogen supply (in the context of examples b1 and b2). The culture temperature was set at 30° C. then 22° C. and finally 18° C. at the end of the culture.

Strain CCAP4062/7 is used for example a and b1 whereas strain FCCB1897 is used for example b2.

The composition of the culture media is given in Table 2.

TABLE 2

|  | a | b1 and b2 |  |
|---|---|---|---|
| CaCl2, 2H2O | 0.55 | 0.55 | g/L |
| MgSO4, 7H2O | 4-8 | 4-8 | g/L |
| H3BO3 | 0.00875-0.175 | 0.00875-0.0175 | g/L |
| K2SO4 | 2.08 | 0.00 | g/L |
| KH2PO4 | 4.00 | 4.00 | g/L |
| Na4EDTA, 2H2O | 0.12 | 0.12 | g/L |
| FeSO4, 7H2O | 0.04 | 0.04 | g/L |
| (NH4)2SO4 | 9.00 | 1.00-2.00 | g/L |
| MnCl2, 4H2O | 0.0108 | 0.0108 | g/L |
| ZnSO4, 7H2O | 0.0108 | 0.0108 | g/L |
| CoCl2, 6H2O | 0.000108 | 0.000108 | g/L |
| Na2MoO4, 2H2O | 0.000108 | 0.000108 | g/L |
| Na2SeO3 | 1.73E-07 | 1.73E-07 | g/L |
| CuSO4, 5H2O | 0.0072 | 0.0072 | g/L |
| NiSO4, 6H2O | 0-0.0056 | 0-0.0056 | g/L |

TABLE 2-continued

|  | a | b1 and b2 |  |
|---|---|---|---|
| Thiamine | 0.0320 | 0.0320 | g/L |
| Vitamin B12 | 0.0005 | 0.0005 | g/L |
| Pantothenate | 0.0108 | 0.0108 | g/L |
| Defoamer Biospumex 153K | 0.40 | 0.40 | mL/L |
| Glucose, 1 H2O | 55.00 | 55.00 | g/L |

Additions of glucose in the form of an enrichment solution are made with a carbon:nitrogen:phosphorus (CNP) molar ratio of 533:11:1 (example a) or with a solution composed only of glucose (examples b1 and b2).

Culture Monitoring:

The total biomass concentration is monitored by measuring the dry mass (filtration on Whatman GF/F filter then oven drying, at 105° C., for a minimum of 24 h before weighing). Fatty acid analyses are carried out according to a method adapted from ISO 12966-2 for the biomass, and according to the European Pharmacopoeia 9.0 (2.4.29) for the oils.

The fatty acid profiles of the biomasses obtained with conditions a, b1 and b2 are given in Table 3. The results are expressed as a percentage of the total fatty acid content.

TABLE 3

|  | a | b1 | b2 |
|---|---|---|---|
| C10:0 | 0.0 | 0.0 | 0.0 |
| C11:0 | 0.0 | 0.0 | 0.0 |
| C12:0 | 0.0 | 0.0 | 0.0 |
| C13:0 | 0.0 | 0.0 | 0.0 |
| C14:0 | 0.8 | 1.2 | 0.3 |
| C14:1 | 0.0 | 0.0 | 0.0 |
| C15:0 | 0.0 | 0.1 | 1.7 |
| C15:1 | 0.0 | 0.0 | 0.0 |
| C16:0 | 13.6 | 19.6 | 10.9 |
| C16:1 | 0.1 | 0.2 | 0.2 |
| C16:2 | 0.0 | 0.0 | 0.0 |
| C16:3 | 0.0 | 0.0 | 0.0 |
| C16:4 | 0.0 | 0.0 | 0.0 |
| C17:0 | 0.0 | 0.0 | 0.0 |
| C17:1 | 0.0 | 0.0 | 0.3 |
| C18:0 | 0.5 | 0.6 | 0.6 |
| C18:1 | 0.2 | 0.3 | 0.4 |
| C18:2 | 0.0 | 0.0 | 0.0 |
| C18:3n3 | 0.2 | 0.1 | 0.2 |
| C18:3n6 | 0.1 | 0.1 | 0.1 |
| C18:4n3 | 0.3 | 0.3 | 0.3 |
| C20:0 | 0.1 | 0.1 | 0.1 |
| C20:4n6 (ARA) | 0.1 | 0.0 | 0.1 |
| C20:5n3 (EPA) | 0.4 | 0.6 | 0.6 |
| C21:0 | 0.0 | 0.1 | 0.0 |
| C22:0 | 0.1 | 0.0 | 0.0 |
| C22:5n3 (DPAn3) | 0.2 | 0.0 | 0.2 |
| C22:5n6 (DPAn6) | 12.9 | 9.6 | 12.7 |
| C22:6n3 (DHA) | 66.6 | 62.5 | 70.1 |
| DHA + DPA | 79.7 | 72 | 83 |
| SFA | 15.1 | 22 | 11.4 |
| DHA/DPA | 5.2 | 6.5 | 5.5 |
| DHA/SFA | 4.4 | 2.9 | 6.2 |
| (DHA + DPA)/SFA | 5.3 | 3.3 | 7.3 |

Example 3: Culture Under Industrial Conditions

High DHA content strains produce a biomass with a similar fatty acid composition when grown in industrial size fermenters, such as 10 m$^3$ or 180 m$^3$ tanks, under conditions similar to example 2, with culture medium b and glucose additions in the form of an enrichment solution are made with a carbon:nitrogen:phosphorus (CNP) molar ratio of 533:0.4:1.

The fatty acid profiles of the CCAP4062/7 strain biomass after culture in 10 m³ and 180 m³ tanks are given in Table 4. The results are expressed as a percentage of the total fatty acid content.

TABLE 4

|  | 10 m³ | 180 m³ |
|---|---|---|
| C10:0 | 0.0 | 0.0 |
| C11:0 | 0.0 | 0.0 |
| C12:0 | 0.0 | 0.0 |
| C13:0 | 0.0 | 0.0 |
| C14:0 | 0.7 | 0.5 |
| C14:1 | 0.0 | 0.0 |
| C15:0 | 0.0 | 0.0 |
| C15:1 | 0.0 | 0.0 |
| C16:0 | 18.1 | 13.6 |
| C16:1 | 0.0 | 0.0 |
| C16:2 | 0.0 | 0.0 |
| C16:3 | 0.0 | 0.0 |
| C16:4 | 0.0 | 0.0 |
| C17:0 | 0.0 | 0.0 |
| C17:1 | 0.0 | 0.0 |
| C18:0 | 0.8 | 0.0 |
| C18:1 | 0.0 | 0.0 |
| C18:2 | 0.0 | 0.0 |
| C18:3n3 | 0.3 | 0.3 |
| C18:3n6 | 0.0 | 0.0 |
| C18:4n3 | 0.0 | 0.0 |
| C20:0 | 0.0 | 0.0 |
| C20:4n6 (ARA) | 0.2 | 0.1 |
| C20:5n3 (EPA) | 0.9 | 0.4 |
| C21:0 | 0.0 | 0.0 |
| C22:0 | 0.0 | 0.0 |
| C22:5n3 (DPAn3) | 0.0 | 0.0 |
| C22:5n6 (DPAn6) | 11.2 | 13.4 |
| C22:6n3 (DHA) | 63.9 | 66.8 |
| DHA + DPA | 75.1 | 80.2 |
| SFA | 19.6 | 14.7 |
| DHA/DPA | 5.3 | 4.8 |
| DHA/SFA | 3.3 | 4.5 |
| (DHA + DPA)/SFA | 3.8 | 5.5 |

Example 4: Extraction of Oil from the Biomass of High DHA Content Strains

The oil is extracted from the biomass of example 3 (180 m³ tank) according to a method described in WO2015/095694 (example 9). The fatty acid composition of the oil is similar to that of the biomass, given in Table 4.

Example 5: Extraction of Oil from the Biomass of High DHA Content Strains

The extraction of the biomass produced under the same conditions as in example 3 is carried out by following the sequence (a) cell lysis by enzymatic means (e.g., with Alcalase 2.5 L or Alcalase 2.4 L or Novozym 37071 from Novozymes) for 4 h at a temperature of 65° C.,
(b) continuation of the lysis by lowering the temperature between 5 and 40° C., for a duration comprised between 30 minutes and 30 h,
(c) mechanical oil separation by centrifugal plate separator.

The extraction yield is 60% lipids extracted from the biomass.

The lipid profile of the oil extracted from the biomass is given in Table 6. The results are expressed as a percentage of the total fatty acid content.

TABLE 6

|  | 10 m³ | 180 m³ |
|---|---|---|
| C10:0 | 0.0 | 0.0 |
| C11:0 | 0.0 | 0.0 |
| C12:0 | 0.0 | 0.0 |
| C13:0 | 0.0 | 0.0 |
| C14:0 | 0.3 | 0.0 |
| C14:1 | 0.0 | 0.0 |
| C15:0 | 0.0 | 0.0 |
| C15:1 | 0.0 | 0.0 |
| C16:0 | 15.3 | 8.3 |
| C16:1 | 0.0 | 0.0 |
| C16:2 | 0.0 | 0.0 |
| C16:3 | 0.0 | 0.0 |
| C16:4 | 0.0 | 0.0 |
| C17:0 | 0.0 | 0.0 |
| C17:1 | 0.0 | 0.0 |
| C18:0 | 0.4 | 0.4 |
| C18:1 | 0.0 | 0.0 |
| C18:2 | 0.0 | 0.0 |
| C18:3n3 | 0.0 | 0.0 |
| C18:3n6 | 0.0 | 0.0 |
| C18:4n3 | 0.0 | 0.0 |
| C20:0 | 0.0 | 0.0 |
| C20:4n6 (ARA) | 0.0 | 0.0 |
| C20:5n3 (EPA) | 0.5 | 0.2 |
| C21:0 | 0.0 | 0.0 |
| C22:0 | 0.0 | 0.0 |
| C22:5n3 (DPAn3) | 0.0 | 0.0 |
| C22:5n6 (DPAn6) | 11.6 | 15.3 |
| C22:6n3 (DHA) | 71.1 | 75 |
| DHA + DPA | 82.7 | 90.3 |
| SFA | 16 | 8.7 |
| DHA/DPA | 5.9 | 4.8 |
| DHA/SFA | 4.4 | 8.6 |
| (DHA + DPA)/SFA | 5.2 | 10.4 |

Example 6: Oil Quality: Antioxidants and Contaminants

Several heterotrophic fermentations are carried out according to the conditions of example 3. The oil is extracted from the fermenting must according to the conditions of example 5. Carotenoids are measured in the extracted oil, by LC/DAD, according to the following methods: Astaxanthin (including ester forms), Reference Method: DSM Ver. 1.5 2009; Beta-carotene (sum of cis- & trans-), saponified, Reference method: EN 12823-2:2000; Canthaxanthin, Reference method: Roche Index No. 2264; Lutein & Zeaxanthin, Reference Method: Roche Index No. 2264.

TABLE 7

|  | Batch No. | | | | |
|---|---|---|---|---|---|
|  | A | B | C | D | E |
| DHA (mg/g FA) | 670 | 674 | 663 | 700 | 707 |
| DHA (% MG) | 70.6 | 71.1 | 70.6 | 72.2 | 72.4 |
| Beta-carotenes (mg/kg FA) | 14 | 14.1 | 13.4 | 11.7 | 11.9 |
| Astaxanthin (mg/kg FA) | 46.1 | 41.4 | 38.2 | 28 | 25.9 |
| Astaxanthin esters (mg/kg FA) | 2 | 4.5 | 4.7 | 4.8 | 5 |
| Canthaxanthin (mg/kg FA) | 3.5 | 3.3 | 3.2 | 3.7 | 3.8 |
| Total carotenoids (mg/kg FA) | 65.6 | 63.3 | 59.6 | 48.3 | 46.6 |
| Gardner index | 14.8 | 16.7 | >18 | 12.3 | 12.3 |
| Anisidine index | 1.17 | 1.13 | 0.54 | 1.35 | 1.97 |
| Peroxide index (meq/kg) | 1 | 0.1 | 0.1 | 1 | 0.1 |

Contaminants such as glycidol and 2- and 3-MCPDs are also assayed in the same batches.

TABLE 8

| | Batch No. | | | | |
|---|---|---|---|---|---|
| | A | B | C | D | E |
| DHA (mg/g FA) | 670 | 674 | 663 | 700 | 707 |
| DHA (% MG) | 70.6 | 71.1 | 70.6 | 72.2 | 72.4 |
| Glycidyl esters (glycidol µg/kg) | <100 | 45 | <100 | <100 | <100 |
| 2-MCPD (free and esters, µg/kg) | <100 | <100 | <100 | <100 | <100 |
| 3-MCPD (free and esters and glycidyl esters) µg/kg | <100 | 210 | <100 | <100 | <100 |

Example 7: Viscosity

The viscosity of the oil produced and extracted under conditions similar to example 5 is measured by a viscometer (Viscoman, Gilson) at different temperatures. The melting temperature is evaluated according to standard ISO 6321.

TABLE 9

| | DHA (mg/g fatty acids-% MG) | Viscosity at 22° C. (Pa·s) | Viscosity at 8° C. (Pa·s) | Viscosity at −20° C. (Pa·s) | Melting temperature (° C.) |
|---|---|---|---|---|---|
| Sample 1 | 582-62 | 50 | >2000 | >2000 | 19 |
| Sample 2 | 634-67 | 39 | >2000 | >2000 | 11 |
| Sample 3 | 689-73 | 31 | 41 | >2000 | <−5° C. |

REFERENCES

EP 0 223 960; EP 1 001 034
US 2014/323569, US 2017/016036, US 2017/335356
WO 1994/008467; WO 1997/037032; WO 2001/054510; WO 03/049832; WO 2010/107415; WO 2012/035262; WO 2013/136025; WO 2013/136028; WO 2014/146098; WO 2015/004402; WO 2015/004403; WO 2015/150716; WO 2016/030631, WO 2017/094804
Fedorova-Dahms I. & al., Safety evaluation of DHA-rich algal oil from *Schizochytrium* sp, Food and Chemical Toxicology, 2011, 49, 3310-3318
Folch J, et al., A simple method for the isolation and purification of total lipides from animal tissues. J Biol Chem. 1957 May; 226(1):497-509
Hamilton M. & al., Heterotrophic Production of Omega-3 Long-Chain Polyunsaturated Fatty Acids by Trophically Converted Marine Diatom *Phaeodactylum tricornum*, Marine Drugs, 2016, 14, 53
Omega-3 long chain fatty acid "bioavailability": a review of evidence and methodological considerations. Ghasemifard S, Turchini G M, Sinclair A J. Prog Lipid Res. 2014 October; 56:92-108. doi: 10.1016/j.plipres.2014.09.001. Epub 2014 Sep. 16. Review.
Wakako TSUZUKI, Study of the Formation of trans Fatty Acids in Model Oils (triacylglycerols) and Edible Oils during the Heating Process, JARQ 46 (3), 215-220 (2012)
Kinuko Miyazaki* and Kazuo Koyama, An Improved Enzymatic Indirect Method for Simultaneous Determinations of 3-MCPD Esters and Glycidyl Esters in Fish Oils, J. Oleo Sci. 66, (10) 1085-1093 (2017)
Jouhet J., Marechal E., Bligny R., Joyard J., Block M. A. (2003). Transient increase of phosphatidylcholine in plant cells in response to phosphate deprivation. FEBS Lett. 544 63-68.

The invention claimed is:

1. A microbial oil extracted from a microbial biomass which comprises docosahexaenoic acid (DHA), wherein the microbial oil comprises
   at least 80% triglycerides in relation to the total mass of fat,
   more than 60% DHA in relation to the total mass of fat, and
   the saturated fatty acid content is less than 25% in relation to the total mass of fat, and wherein the microbial oil has not undergone substantial modification of its fatty acid content by the addition of polyunsaturated fatty acids, by concentration and/or by the removal of saturated fatty acids.

2. The microbial oil according to claim 1, wherein the microbial oil comprises at least 65% DHA in relation to the total mass of fat.

3. The microbial oil according to claim 1 wherein the microbial oil comprises docosapentaenoic acid (DPA) and the combined DHA and DPA content in the microbial oil is at least 70% in relation to the total mass of fat.

4. The microbial oil according to claim 1, wherein the microbial oil comprises at least 70% DHA.

5. The microbial oil according to claim 4, wherein the microbial oil comprises docosapentaenoic acid (DPA) and the combined DHA and DPA content in the microbial oil is at least 80% in relation to the total mass of fat.

6. The microbial oil according to claim 1, wherein the microbial oil comprises docosapentaenoic acid (DPA) and the DHA/DPA ratio in the microbial oil is at least 4.

7. The microbial oil according to claim 1, wherein the saturated fatty acid content in the microbial oil is less than 15% in relation to the total mass of fat.

8. The microbial oil according to claim 1, wherein the microbial oil has a viscosity at room temperature of 50 Pa·s or less.

9. The microbial oil according to claim 8, wherein the microbial oil has a viscosity of less than 30 Pa·s.

10. A diluted microbial oil, wherein the diluted oil comprises a microbial oil according to claim 1, mixed with another oil.

11. A biomass of microorganisms, obtained by industrial culture of the microorganisms and comprising an oil wherein the oil comprises docosahexaenoic acid (DHA), and wherein the oil comprises:
    at least 80% triglycerides in relation to the total mass of fat,
    more than 60% DHA in relation to the total mass of fat, and
    the saturated fatty acid content is less than 25% in relation to the total mass of fat.

12. A food, wherein said food comprises the microbial oil according to claim 1.

13. The microbial oil according to claim 1, wherein the microbial oil comprises less than 0.5% of arachidonic acid (ARA) in relation to the total mass of fat.

14. The microbial oil according to claim 1, wherein the microbial oil comprises less than 1.5% of eicosapentaenoic acid (EPA) in relation to the total mass of fat.

15. The microbial oil according to claim 1, wherein the microbial oil has a melting temperature below −5° C.

16. The biomass of microorganism according to claim 11, wherein the microbial oil in the biomass comprises at least 70% DHA in relation to the total mass of fat.

17. The biomass of microorganisms according to claim 11, wherein the microbial oil in the biomass comprises docosapentaenoic acid (DPA) and the combined DHA and DPA content in the microbial oil is at least 80% in relation to the total mass of fat.

18. The biomass of microorganisms according to claim 11, wherein the microbial oil in the biomass comprises docosapentaenoic acid (DPA) and the DHA/DPA ratio in the microbial oil is at least 4.

19. The microbial oil according to claim 1, wherein the microbial oil has a palmitic acid (C16:0) content lower than 10% in relation to the total mass of fat.

20. The microbial oil according to claim 1, wherein the microbial oil is a crude oil or a refined oil.

21. The microbial oil according to claim 1, wherein the microbial oil is in quantity higher than 1 L and is packaged in a container whose volume is equal to or greater than that of the oil so as to limit the presence of air in the container and limit oxidation.

* * * * *